(12) United States Patent
Saoji et al.

(10) Patent No.: US 8,321,026 B2
(45) Date of Patent: Nov. 27, 2012

(54) SPECTRAL TILT OPTIMIZATION FOR COCHLEAR IMPLANT PATIENTS

(75) Inventors: Aniket Saoji, Northridge, CA (US); Leonid M. Litvak, Los Angeles, CA (US)

(73) Assignee: Advanced Bionics, LLC, Valencia, CA (US)

( * ) Notice: Subject to any disclaimer, the term of this patent is extended or adjusted under 35 U.S.C. 154(b) by 485 days.

(21) Appl. No.: 12/556,972

(22) Filed: Sep. 10, 2009

(65) Prior Publication Data

US 2010/0069998 A1  Mar. 18, 2010

Related U.S. Application Data

(60) Provisional application No. 61/096,700, filed on Sep. 12, 2008.

(51) Int. Cl.
 *A61N 1/05* (2006.01)
(52) U.S. Cl. ........................................................ 607/55
(58) Field of Classification Search ............... 607/55–57
See application file for complete search history.

(56) References Cited

U.S. PATENT DOCUMENTS

| | | | |
|---|---|---|---|
| 2006/0178711 A1 | 8/2006 | Patrick et al. | |
| 2006/0235332 A1* | 10/2006 | Smoorenburg | 600/559 |
| 2007/0135862 A1* | 6/2007 | Nicolai et al. | 607/56 |

OTHER PUBLICATIONS

Zeng, et al., "Cochlear Implants: System Design, Integration, and Evaluation", *Reviews in Biomedical Engineering*, Jan. 1, 2008.
International Search Report and Written Opinion received in International Application No. PCT/US2009/056488, Nov. 20, 2009.

* cited by examiner

*Primary Examiner* — Carl H Layno
*Assistant Examiner* — Allen Porter, Jr.
(74) *Attorney, Agent, or Firm* — AdvantEdge Law Group, LLC (57) ABSTRACT

Methods and systems of spectral tilt optimization for a cochlear implant patient include applying electrical stimulation representative of an audio signal to a patient in accordance with a spectral tilt value and optimizing the spectral tilt value in response to a measured ability of the patient to recognize at least one attribute of the audio signal.

18 Claims, 11 Drawing Sheets

SPECTRAL TILT OPTIMIZATION FOR COCHLEAR IMPLANT PATIENTS

RELATED APPLICATIONS

The present application claims priority under 35 U.S.C. §119(e) to U.S. Provisional Patent Application No. 61/096,700 by Aniket Saoji et al., filed on Sep. 12, 2008, and entitled "SPECTRAL TILT OPTIMIZATION FOR COCHLEAR IMPLANT PATIENTS," the contents of which are hereby incorporated by reference in their entirety.

BACKGROUND

The sense of hearing in human beings involves the use of hair cells in the cochlea that convert or transduce audio signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be helped by the use of conventional hearing aids that amplify sound so that audio signals reach the cochlea and the hair cells. Some types of conductive hearing loss may also be treated by surgical procedures.

Sensorineural hearing loss, on the other hand, is due to the absence or the destruction of the hair cells in the cochlea which are needed to transduce audio signals into auditory nerve impulses. Thus, many people who suffer from severe to profound sensorineural hearing loss are unable to derive any benefit from conventional hearing aid systems.

To overcome sensorineural hearing loss, numerous cochlear implant systems—or cochlear prosthesis—have been developed. Cochlear implant systems bypass the hair cells in the cochlea by presenting electrical stimulation directly to the auditory nerve fibers. Direct stimulation of the auditory nerve fibers leads to the perception of sound in the brain and at least partial restoration of hearing function. To facilitate direct stimulation of the auditory nerve fibers, an array of electrodes may be implanted in the cochlea. The electrodes form a number of stimulation channels through which electrical stimulation pulses may be applied directly to auditory nerves within the cochlea.

Hence, an audio signal may be presented to a patient by processing and translating the audio signal into a number of electrical stimulation pulses. The stimulation pulses may then be applied directly to auditory nerves within the cochlea via one or more of the stimulation channels. However, in traditional cochlear implants, important information from an audio signal can be lost during translation of the audio signal into electrical stimulation pulses. Such losses during translation may make it difficult for cochlear implant patients to enjoy the full advantages of the cochlear implant. For example, losses during translation may make it difficult for cochlear implant patients to identify a speaker, recognize speech, and appreciate the nuances of musical sound.

SUMMARY

Methods of spectral tilt optimization for a cochlear implant patient include applying electrical stimulation representative of an audio signal to a patient in accordance with a spectral tilt value and optimizing the spectral tilt value in response to a measured ability of the patient to recognize at least one attribute of the audio signal.

Systems for spectral tilt optimization for a cochlear implant patient include a sound processor communicatively coupled to an implantable cochlear stimulator. The implantable cochlear stimulator is configured to apply electrical stimulation representative of an audio signal to a patient in accordance with a spectral tilt. The sound processor is configured to adjust the spectral tilt in response to a measured ability of the patient to recognize at least one attribute of the audio signal.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

Throughout the drawings, identical reference numbers designate similar, but not necessarily identical, elements.

DETAILED DESCRIPTION

Methods and systems for optimizing a spectral tilt value corresponding to an audio signal applied to a cochlear implant patient are described herein. In some examples, an implantable cochlear stimulator is configured to apply electrical stimulation representative of an audio signal to a patient in accordance with a spectral tilt value. A sound processor is communicatively coupled to the implantable cochlear stimulator and configured to optimize the spectral tilt in response to a measured ability of the patient to recognize at least one attribute of the audio signal.

In some examples, a programming device is selectively and communicatively coupled to the sound processor. The programming device may be configured to direct the sound processor to generate a plurality of spectral tilt values. The programming device may record a recognition score achieved by the patient for each of the plurality of spectral tilt values, wherein the recognition score corresponds to an ability of the patient to recognize at least one attribute of the audio signal applied in accordance with each of the spectral tilt values. The programming device may be further configured to select one of the spectral tilt values as an optimal spectral tilt value for the patient based on the recorded recognition scores.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one example" or "an example" means that a particular feature, structure, or characteristic described in connection with the example is included in at least one example. The appearance of the phrase "in one example" in various places in the specification are not necessarily all referring to the same example.

Figure 1:
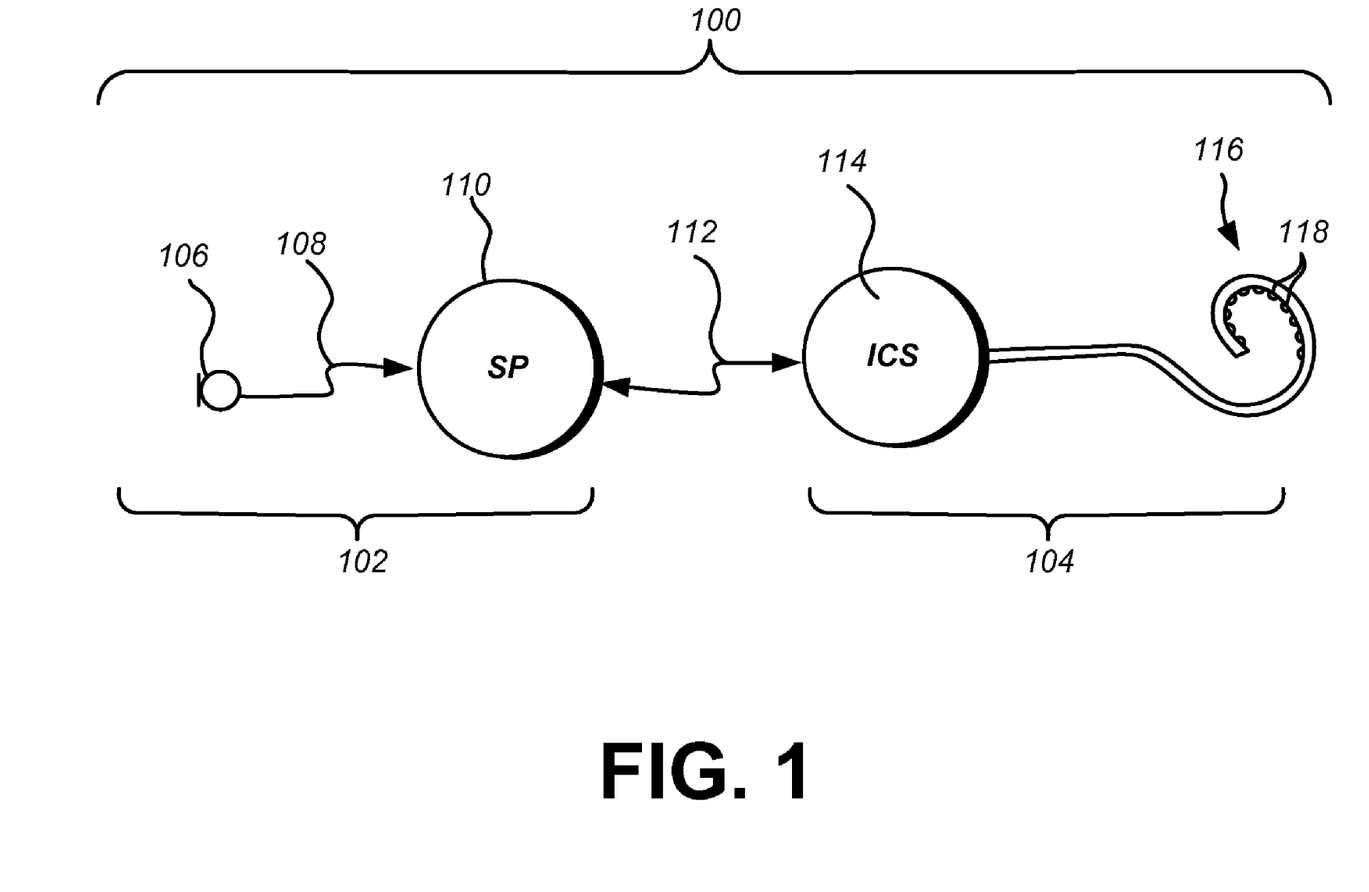
FIG. 1 illustrates an exemplary cochlear implant system according to principles described herein.

FIG. 1 illustrates an exemplary cochlear implant system 100 that may be used in accordance with the present methods and systems. The cochlear implant system 100 of FIG. 1 includes a sound processor portion 102 and a cochlear stimulation portion 104. The sound processor portion 102 may include a sound processor 110, a microphone 106, and/or additional circuitry as best serves a particular application. The cochlear stimulation portion 104 may include an implantable cochlear stimulator 114, a number of electrodes 118 disposed on a lead 116, and/or additional circuitry as best serves a particular application. The components within the sound processor portion 102 and the cochlear stimulation portion 104 will be described in more detail below.

The microphone 106 of FIG. 1 is configured to sense audio signals and convert the sensed signals to corresponding electrical signals. In some examples, the audio signal may include speech. The audio signal may additionally or additionally include music, noise, and/or other sounds. The electrical signals are sent from the microphone 106 to the sound processor 110 via a communication link 108. Alternatively, the microphone 106 may be connected directly to, or integrated with, the sound processor 110.

The sound processor 110 processes these converted audio signals in accordance with a selected sound processing strategy to generate appropriate stimulation parameters for controlling the implantable cochlear stimulator 114. These stimulation parameters may specify or define the polarity, magnitude, location (i.e., which electrode pair or electrode group receive the electrical stimulation), stimulation rate, timing (i.e., when the electrical stimulation is to be applied to a particular electrode pair), spectral tilt, and/or any other characteristic of the electrical stimulation that is generated by the implantable cochlear stimulator 114. To facilitate processing of the converted audio signals, sound processor 110 may include any combination of hardware, software, and/or firmware. For example, sound processor 110 may include one or more processors (e.g., digital signal processors), memory having one or more software applications residing therein, and/or any other component as may serve a particular application.

The lead 116 shown in FIG. 1 is configured to be inserted within a duct of a cochlea. As shown in FIG. 1, the lead 116 includes a multiplicity of electrodes 118, e.g., sixteen electrodes, spaced along its length. It will be understood, however, that any number of electrodes 118 may be disposed on the lead 116. As will be described in more detail below, electronic circuitry within the implantable cochlear stimulator 114 is configured to generate and apply electrical stimulation to one or more stimulation sites within the cochlea via selected stimulation channels (i.e., pairs or groups of the individual electrodes 118) in accordance with a specified stimulation strategy defined by the sound processor 110.

The implantable cochlear stimulator 114 and the sound processor 110 may be communicatively coupled via a suitable data or communication link 112. It will be understood that the data communication link 112 may include a bi-directional communication link and/or one or more dedicated unidirectional communication links.

In some examples, the sound processor 110 and the microphone 106 comprise an external portion of the cochlear implant system 100 and the implantable cochlear stimulator 114 and the electrode lead 116 comprise an implantable portion of the system 100 that is implanted within a patient's body. In alternative embodiments, one or more portions of the sound processor 110 are included within the implantable portion of the cochlear implant system 100.

The external and implantable portions of the cochlear implant system 100 may each include one or more coils configured to transmit and receive power and/or control signals via the communication link 112. For example, the external portion of the cochlear implant system 100 may include an external coil (not shown) and the implantable portion of the cochlear implant system 100 may include an implantable coil (not shown). The external coil and the implantable coil may be inductively coupled to each other, thereby allowing data to be transmitted therebetween. The data may include, for example, the magnitude and polarity of a sensed audio signal. The external coil may also transmit power from the external portion to the implantable portion of the cochlear implant system 100.

It will be noted that, in some embodiments, both the sound processor 110 and the implantable cochlear stimulator 114 may be implanted within the patient, either in the same housing or in separate housings. If the sound processor 110 and the implantable cochlear stimulator 114 are in the same housing, the communication link 112 may be realized with a direct wire connection within such housing. If the sound processor 110 and the implantable cochlear stimulator 114 are in separate housings, the communication link 112 may include one or more inductive links, for example.

Figure 2:
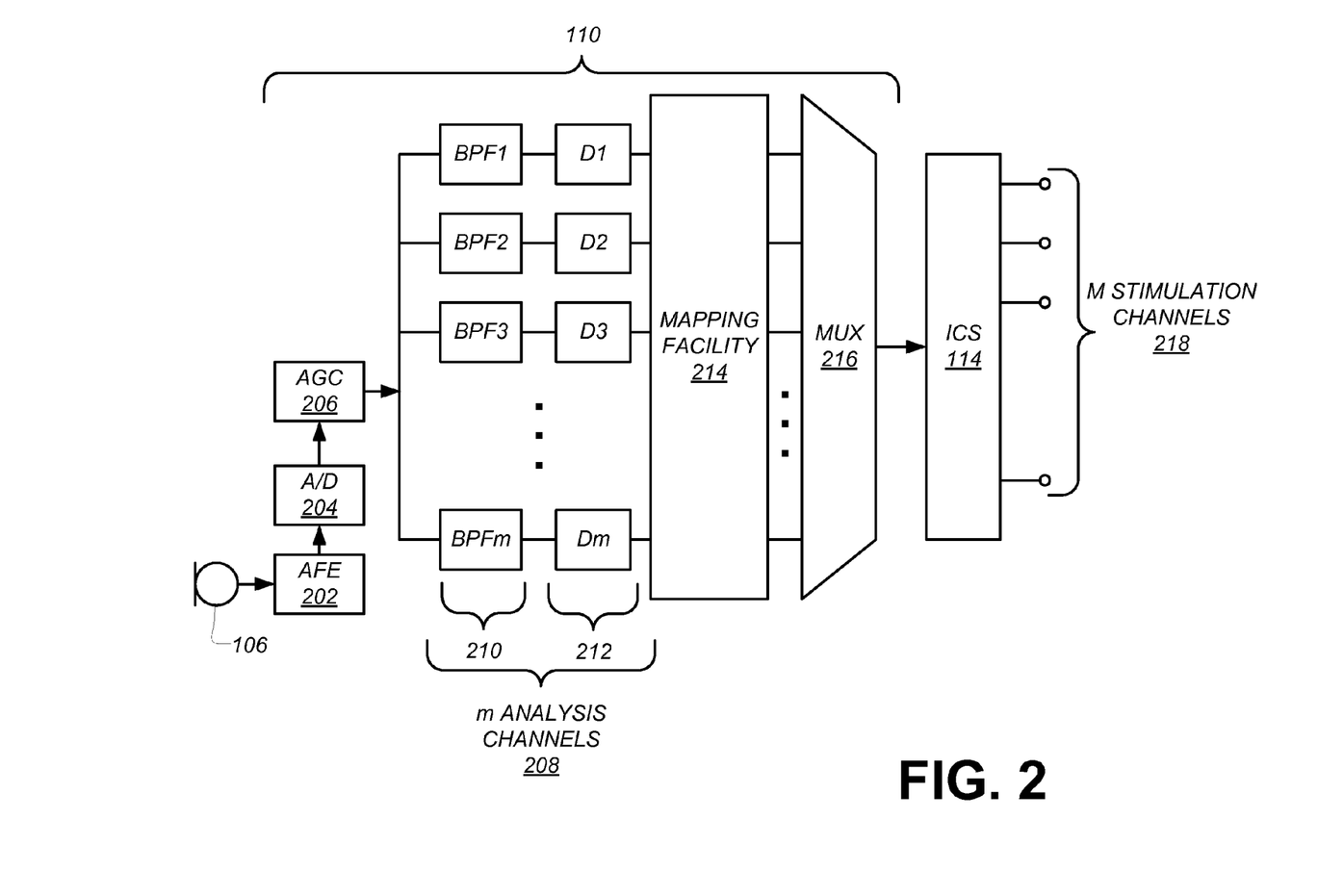
FIG. 2 is a functional block diagram of an exemplary sound processor and implantable cochlear stimulator according to principles described herein.

FIG. 2 is a functional block diagram of an exemplary sound processor 110 and implantable cochlear stimulator 114. The functions shown in FIG. 2 are merely representative of the many different functions that may be performed by the sound processor 110 and/or the implantable cochlear stimulator 114.

As shown in FIG. 2, the microphone 106 senses an audio signal, such as speech or music, and converts the audio signal into one or more electrical signals. These signals are then amplified in audio front-end (AFE) circuitry 202. The amplified audio signal is then converted to a digital signal by an analog-to-digital (A/D) converter 204. The resulting digital signal is then subjected to automatic gain control using a suitable automatic gain control (AGC) module 206.

After appropriate automatic gain control, the digital signal is then processed in one of a number of digital signal processing or analysis channels 208. For example, the sound processor 110 may include, but is not limited to, eight analysis channels 208. Each analysis channel 208 may respond to a different frequency band of the sensed audio signal due to a series of band pass filters 210.

As shown in FIG. 2, each of the m analysis channels 208 may also include an energy detection stage (D1-Dm) 212. Each energy detection stage 212 may include any combination of circuitry configured to detect the amount of energy contained within each of the m analysis channels 208. For example, each energy detection stage 212 may include a rectification circuit followed by an integrator circuit.

After energy detection, the signals within each of the m analysis channels 208 are forwarded to a mapping facility 214. The mapping facility 214 may include any combination of hardware, software, and/or firmware and may be configured to map the signals in each of the m analysis channels 208 to one or more of M stimulation channels 218. In other words, the information contained in the m analysis channels 208 is used to define the electrical stimulation pulses that are applied to the patient by the implantable cochlear stimulator 114 via the M stimulation channels 218. As mentioned previously, pairs or groups of individual electrodes 118 may make up the M stimulation channels 218.

In some examples, the mapped signals are serialized by a multiplexer 216 and transmitted to the implantable cochlear stimulator 114. The implantable cochlear stimulator 114 may then apply electrical stimulation via one or more of the M stimulation channels 218 to one or more stimulation sites within the duct of the patient's cochlea. As used herein, the term "stimulation site" will be used to refer to a target area or location to which the electrical stimulation is applied. For example, a stimulation site may refer to any location within a region of auditory nerve tissue shown in FIG. 3.

Figure 3:
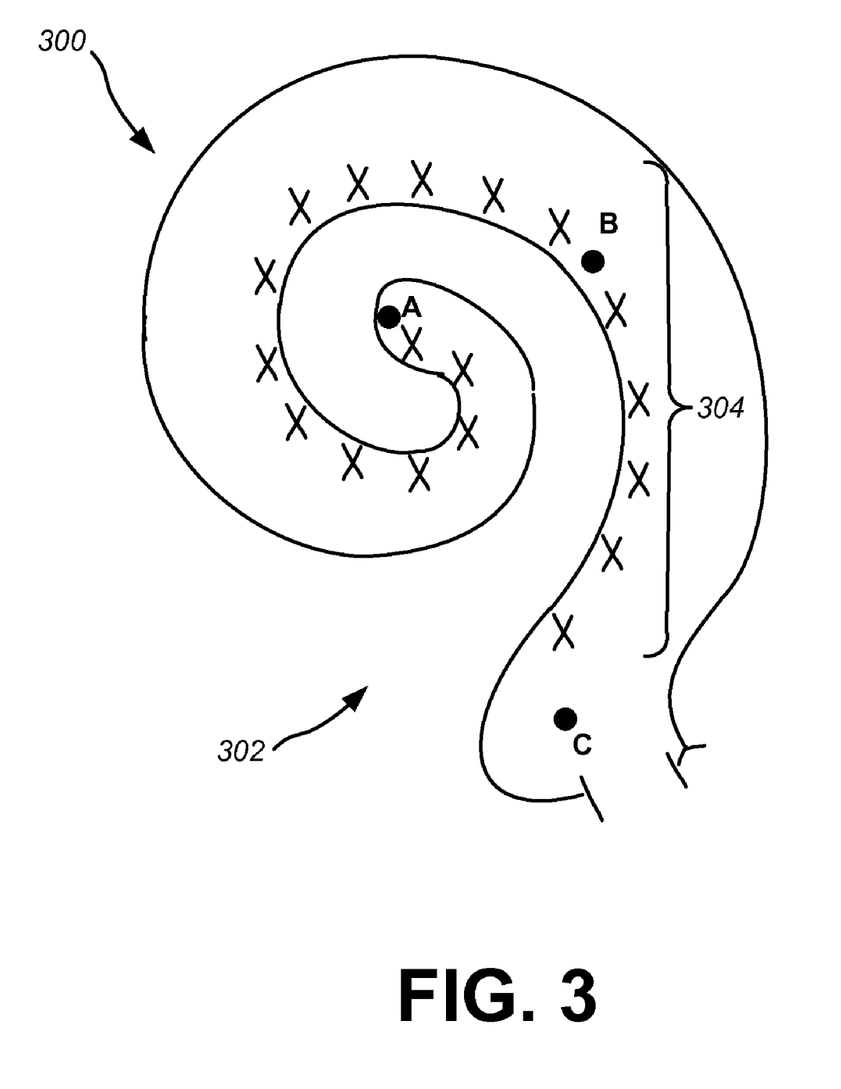
FIG. 3 illustrates a schematic structure of the human cochlea highlighting elements according to principles described herein.

FIG. 3 illustrates a schematic structure of the human cochlea 300. The cochlea 300 includes a duct 302. The section of the cochlea 300 and of the duct 302 from point A to point B, i.e., section AB, has a spiral shape. In contrast, the section from point B to point C, i.e., section BC, is substantially straight.

On the other side of the outside wall of the duct 302 resides auditory nerve tissue 304, that, when stimulated, conveys sound information to the brain. The region of this auditory nerve tissue 304 is denoted by Xs in FIG. 3. Each location within the auditory nerve tissue 304 corresponds to a different perceived frequency or pitch. For example, stimulation of locations in the auditory nerve tissue 304 closer to point A causes the patient to perceive relatively low frequencies, while stimulation of locations closer to point C causes the patient to perceive relatively high frequencies. In patients with sensorineural hearing loss, a cochlear implant system, such as cochlear implant system 100, can electrically stimulate stimulation sites within the auditory nerve tissue 304 at specific frequency locations to provide the sensation of hearing.

When a cochlear implant system 100 is initially implanted in a patient, and during follow-up tests and checkups thereafter, it is often necessary to fit the cochlear implant system 100 to the patient. Such "fitting" includes adjustment of one or more stimulation parameters that define the electrical stimulation that is applied by the cochlear implant system 100 to the patient.

The effectiveness of a cochlear implant system 100 is at least in part dependent on the physiological characteristics of the patient. Hence, a particular set of stimulation parameters may be optimal for one patient and sub-optimal for another. Moreover, the optimal stimulation parameters for a particular patient may vary during the patient's lifetime.

Additionally or alternatively, the effectiveness of a cochlear implant system 100 may be dependent on a listening environment of the user. For example, a user may adequately detect speech and/or other sounds in a quiet environment, but have difficulties detecting speech and/or other sounds in a noisy environment.

One of the stimulation parameters that may be specified during a fitting session is a "spectral tilt" of the electrical stimulation that is applied to the patient. As used herein, "spectral tilt" refers to a variation in intensity or gain across a range of frequencies of electrical stimulation applied via a plurality of stimulation channels 218. Spectral tilt may be realized by adjusting a gain of each individual stimulation channel 218 or electrode 118 corresponding to a particular frequency such that a gain-to-electrode function may be represented as a line with a certain slope within the frequency domain. Hence, spectral tilt is represented by the slope of the gain-to-electrode function.

Figure 4A:
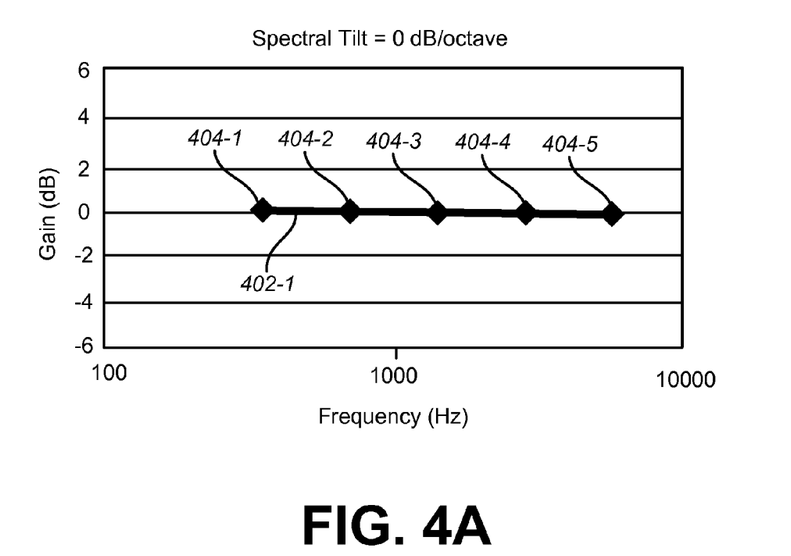
FIGS. 4A-4C illustrate exemplary gain-to-electrode functions each having a distinct spectral tilt within an input frequency spectrum according to principles described herein.
Figure 4B:
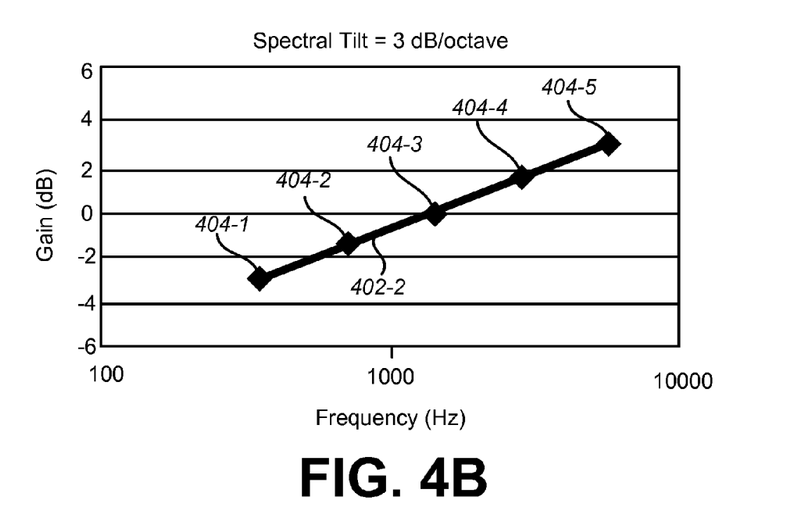
Figure 4C:
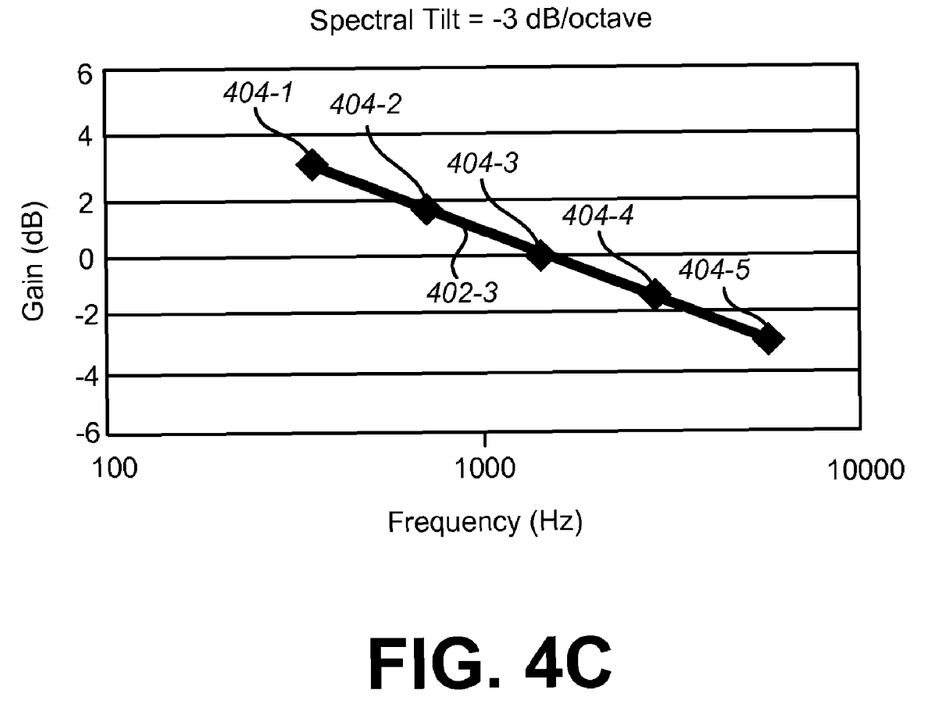

FIGS. 4A-4C illustrate exemplary gain-to-electrode functions 402-1 through 402-3, collectively referred to herein as "gain-to-electrode functions 402", each having a distinct spectral tilt within an input frequency spectrum. As mentioned, each electrode 118 located within a cochlea may correspond to a particular stimulation channel 218 and frequency. Hence, as shown in FIGS. 4A-4C, the gain-to-electrode functions 402 may be represented in the frequency domain, where each electrode 118 may correspond to a particular frequency shown in the horizontal axes.

As shown in FIGS. 4A-4C, a number of data points 404-1 through 404-5 (collectively referred to herein as "data points 404") are superimposed on the lines representing the gain-to-electrode functions 402. Each data point 404 may represent a particular electrode 118 disposed at a particular location within the cochlea. It will be assumed in the examples given herein that each electrode 118 corresponds to a distinct stimulation channel 218. However, it will be recognized that any number of electrodes 118 comprising any number of stimulation channels 218 may be located within the cochlea as may serve a particular application.

The electrical stimulation applied via each individual electrode 118 may have an adjustable intensity or gain. Hence, each gain-to-electrode function 402 represents a relationship between gain and each electrode 118 included within a cochlear implant system 100. This gain may be measured in decibels (dB) and is represented by the vertical axes shown in FIGS. 4A-4C.

As shown in FIGS. 4A-4C, each gain-to-electrode function 402 has a certain slope, which represents spectral tilt. Spectral tilt may be measured in decibels per octave (dB/octave). For example, the gain-to-electrode function 402-1 shown in FIG. 4A has a spectral tilt of 0 dB/octave, the gain-to-electrode function 402-2 shown in FIG. 4B has a spectral tilt of 3 dB/octave, and the gain-to-electrode function 402-3 shown in FIG. 4C has a spectral tilt of −3 dB/octave.

In some examples, spectral tilt of a gain-to-electrode function 402 may be adjusted by adjusting one or more gain parameters corresponding to each electrode 118. For example, the spectral tilt corresponding to an input audio signal may initially be 0 dB/octave, as shown in FIG. 4A. To change the spectral tilt to 3 dB/octave, as shown in FIG. 4B, the gain of each electrode 118 corresponding to relatively low frequencies may be decreased and the gain of each electrode 118 corresponding to relatively high frequencies may be increased. Such adjustment of the gain parameters may be correlated to ensure that the gain-to-electrode function remains linear. For example, a spectral tilt may be adjusted by pivoting a gain-to-electrode function 402 about a particular center frequency.

The particular spectral tilt used in connection with an input audio signal may affect the ability of a patient to recognize speech, appreciate music, or hear other sounds. Hence, it is desirable to optimize spectral tilt when a cochlear implant system 100 is fitted to a patient and/or any time thereafter.

However, because each patient has a unique set of physiological characteristics, the optimal spectral tilt may vary from patient to patient. For example, an optimal spectral tilt for a particular patient may be −2 dB/octave while an optimal spectral tilt for another patient may be 1 dB/octave. Moreover, an optimal spectral tilt for a patient may vary depending on the listening environment of the patient. For example, an optimal spectral tilt for a patient in a noisy environment may be different than an optimal spectral tilt for the patient in a quiet environment.

Figure 5:
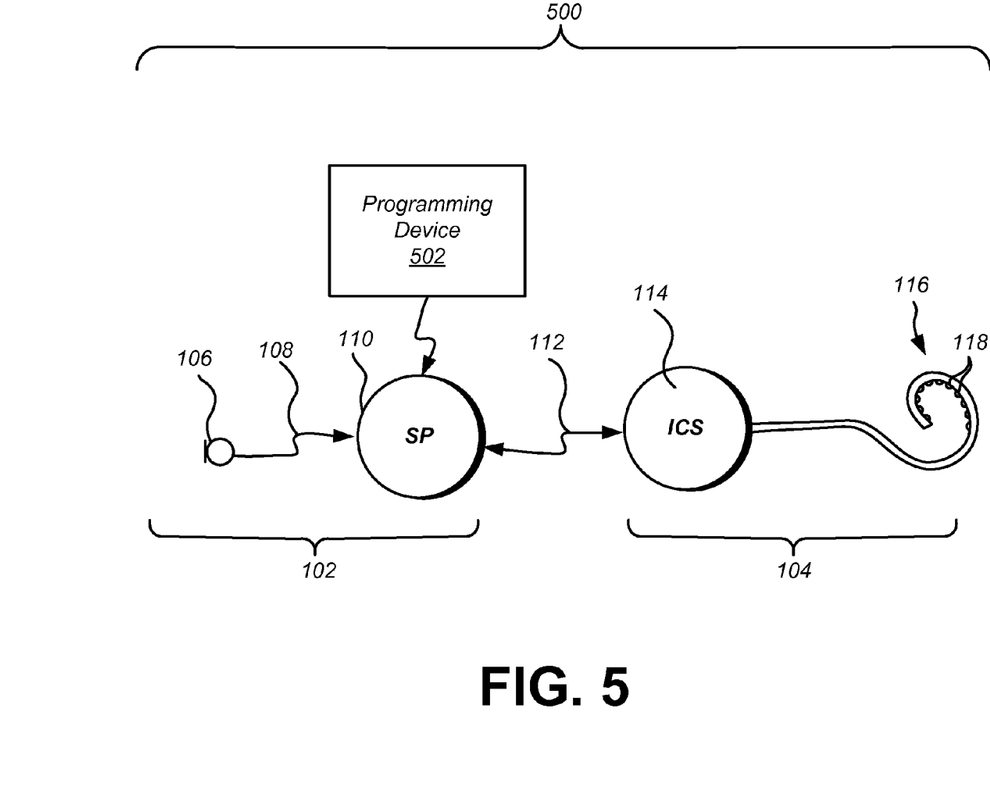
FIG. 5 illustrates an exemplary system configured to facilitate spectral tilt optimization based at least in part on the physiological characteristics and/or the listening environment of a patient according to principles described herein.

Hence, the systems and methods described herein facilitate patient-specific spectral tilt optimization based at least in part on the physiological characteristics and/or the listening environment of the patient. FIG. 5 illustrates an exemplary system 500 configured to facilitate patient-specific spectral tilt optimization based at least in part on the physiological characteristics and/or the listening environment of the patient.

As shown in FIG. 5, a programming device 502 may be selectively and communicatively coupled to sound processor 110. The programming device 502 may include any combination of hardware, software, and firmware configured to perform any of the functions described herein. For example, the programming device 502 may include a fitting station, personal computer, handheld device (e.g., a personal digital assistant), a mobile device (e.g., a mobile telephone), and/or any other computing device as may serve a particular application. As will be described in more detail below, the programming device 502 may be configured to direct cochlear implant system 100 to apply electrical stimulation representative of an audio signal to a cochlear implant patient in accordance with a plurality of different spectral tilts corresponding to the audio signal, record one or more recognition scores representing an ability of the patient to recognize at least one attribute of the audio signal at each spectral tilt value, and select an optimal spectral tilt value for the patient in accordance with the recorded recognition scores.

Figure 6:
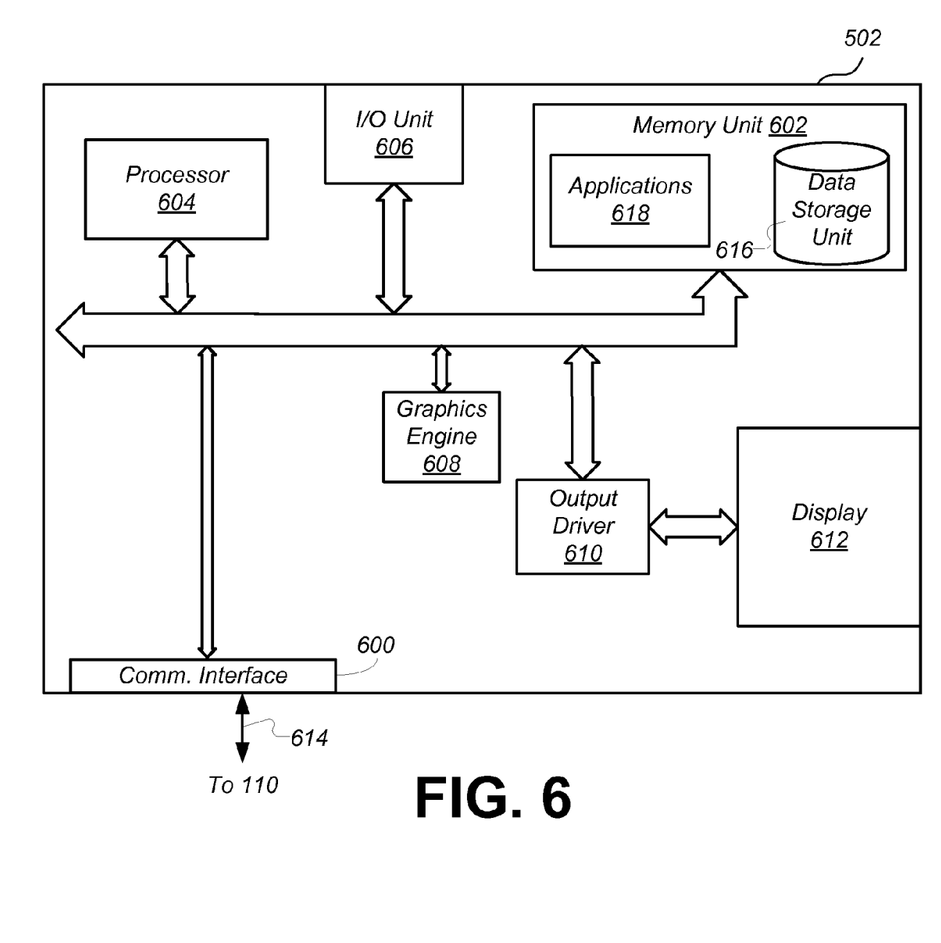
FIG. 6 illustrates a number of components that may be included within an exemplary programming device according to principles described herein.

FIG. 6 illustrates a number of components that may be included within an exemplary programming device 502. While an exemplary programming device 502 is shown in FIG. 6, the exemplary components illustrated in FIG. 6 are not intended to be limiting. Indeed, additional or alternative components and/or implementations may be included within the programming device 502.

In general, the programming device 502 may include any device configured to be selectively and communicatively coupled to one or more components of the cochlear implant system 100. For example, the programming device 502 may be selectively and communicatively coupled to the sound processor 110. Programming device 502 may also be configured to interact with various peripherals such as a terminal, keyboard, mouse, display screen, printer, stylus, input device(s), output device(s), and/or any other apparatus(es).

As shown in FIG. 6, the programming device 502 may include a communication interface 600, programmable memory unit 602, processor 604, input/output unit 606 ("I/O unit 606"), graphics engine 608, output driver 610, and display 612 communicatively connected to one another.

Communication interface 600 may be configured to transmit and receive data to and from the sound processor 110. Exemplary data transmitted from the programming device 502 to the sound processor 110 includes programming data such as stimulation parameters and the like. Exemplary data received by the programming device 502 from the sound processor 110 includes status data representative of a status of one or more components of the sound processor 110 and/or the implantable cochlear stimulator 114.

In some examples, a communications link 614 may be used to facilitate communication between the programming device 502 and the sound processor 110. The communications link 614 may include any type of link used to transmit data, such as, but not limited to, an RF link, an infrared (IR) link, an optical link, a Bluetooth link, a thermal link, a wire link, or any other suitable link.

Programmable memory unit 602 may include, but is not limited to, FLASH memory, RAM, DRAM, or a combination thereof. The programmable memory unit 602 may additionally or alternatively include a data storage unit 616. The data storage unit 616 may include one or more data storage media, devices, or configurations and may employ any type, form, and combination of storage media. For example, the data storage unit 616 may include, but is not limited to, a hard drive, flash drive, optical disk, or other non-volatile storage unit. Log data corresponding to one or more recorded recognition scores and/or any other data may be stored within the data storage unit 616.

Processor 604 may be configured to control one or more operations of the components included within the programming device 502. Processor 604 may direct execution of operations in accordance with computer-executable instructions such as may be stored in memory unit 602. As an example, processor 604 may be configured to process log data corresponding to one or more recognition scores and adjust a spectral tilt value accordingly.

I/O unit 606 may be configured to receive user input and provide user output and may include any hardware, firmware, software, or combination thereof supportive of input and output capabilities.

As instructed by processor 604, graphics engine 608 may generate graphics, which may include graphical user interfaces ("GUIs"). The output driver 610 may provide output signals representative of the graphics generated by graphics engine 608 to display 612. The display 612 may then present the graphics to the user.

One or more applications 618 may be executed by the programming device 502. The applications, or application clients, may reside in memory unit 602 or in any other area of the programming device 502 and be executed by the processor 604. Each application 618 may correspond to a particular feature or capability of the programming device 502. For example, illustrative applications 618 may include one or more of a GUI application, data processing application, and/or stimulation parameter generation application.

It will be recognized that one or more processes and/or applications described herein may be implemented at least in part as computer-executable instructions, i.e., instructions executable by one or more computing devices, tangibly embodied in a computer-readable medium. In general, a processor (e.g., a microprocessor) receives instructions, e.g., from a memory, a computer-readable medium, etc., and executes those instructions, thereby performing one or more processes, including one or more of the processes described herein. Such instructions may be stored and transmitted using a variety of known computer-readable media.

A computer-readable medium (also referred to as a processor-readable medium) includes any medium that participates in providing data (e.g., instructions) that may be read by a computer (e.g., by a processor of a computer). Such a medium may take many forms, including, but not limited to, non-volatile media, volatile media, and transmission media. Non-volatile media may include, for example, optical or magnetic disks and other persistent memory. Volatile media may include, for example, DRAM, which typically constitutes a main memory. Transmission media may include, for example, coaxial cables, copper wire and fiber optics, including the wires that comprise a system bus coupled to a processor of a computer. Transmission media may include or convey acoustic waves, light waves, and electromagnetic emissions, such as those generated during RF and infrared IR data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

As mentioned, programming device 502 may be configured to direct cochlear implant system 100 to apply electrical stimulation representative of an audio signal to a cochlear implant patient while varying a spectral tilt value corresponding to the audio signal. The audio signal may contain speech, music, or other sounds as may serve a particular application and may include one or more recognizable attributes such as, but not limited to, words, lyrics, notes, musical patterns, harmonic relationships, pitches, and/or noises. It will be assumed in the examples given herein that the audio signal includes speech.

In some examples, the audio signal may simulate and/or exemplify one or more listening environments that the patient may experience. For example, if the patient complains of hearing in nosy environments, the noise may be added to pre-recorded speech and presented to the patient in order to determine an optimal spectral tilt value for the noisy environment.

In some examples, the programming device 502 may be configured to repeatedly apply the same audio signal to the patient each time the spectral tilt is adjusted to a new value. Alternatively, the spectral tilt may be periodically adjusted to a new value while a particular audio signal is continuously applied to the patient.

Programming device 502 may be configured to facilitate recording of a recognition score attained by the patient for each spectral tilt value. As used herein, "recognition score" refers to a measured ability of a patient to recognize at least one attribute of an audio signal. For example, a recognition score may represent an ability of a patient to correctly identify one or more words included within the audio signal.

Figure 7:
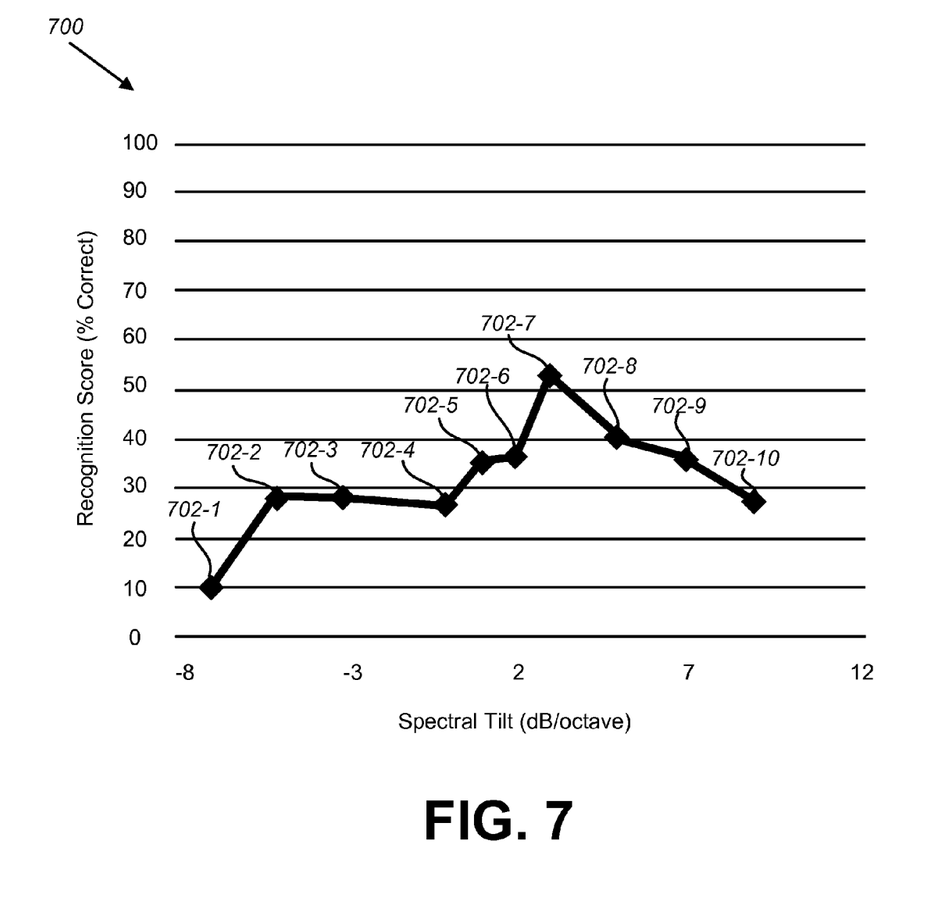
FIG. 7 depicts a graph showing a relationship between recognition scores and spectral tilt for a particular patient according to principles described herein.

To illustrate, FIG. 7 depicts a graph 700 showing a relationship between recognition scores and spectral tilt for a particular patient. As shown in FIG. 7, the horizontal axis represents spectral tilt measured in dB/octave and the vertical axis represents recognition scores measured in percent correct. In other words, the recognition scores shown in FIG. 7 correspond to a percentage of words included within an audio signal that are correctly recognized by the patient. The recognition scores may be alternatively measured in any other way as may serve a particular application.

As shown in FIG. 7, a plurality of recognition scores 702-1 through 702-10 (collectively referred to herein as "recognition scores 702") each corresponding to a particular spectral tilt value are plotted within graph 700. Each recognition score 702 may be recorded by programming device 502 in response to clinician input and/or automatically in response to patient feedback. For example, a speech recognition test may be performed each time the audio signal is applied to the patient with a new spectral tilt. The speech recognition test may be configured to determine a number of words contained within the audio signal that are correctly identified by the patient. By dividing the number of words correctly identified by the total number of words contained within the audio signal, a recognition score measured in percent correct may be obtained. The number of spectral tilts values included within the speech recognition test may vary as may serve a particular application. Moreover, the order in which the spectral tilt values are tested may also vary as may serve a particular application.

FIG. 7 shows that recognition scores corresponding to a particular patient may vary across a range of spectral tilt values. To illustrate, FIG. 7 shows that a spectral tilt of approximately −7 dB/octave resulted in the patient obtaining a recognition score of approximately 10 percent while a spectral tilt of approximately 3 dB/octave resulted in the patient obtaining a recognition score of over 50 percent.

In some examples, an optimal spectral tilt value corresponds to a spectral tilt value that results in the highest recognition score achieved by a patient. To illustrate, in the example of FIG. 7, a spectral tilt of approximately 3 dB/octave corresponds to the maximum recognition score achieved by the cochlear implant patient. Hence, the spectral tilt may be adjusted to 3 dB/octave to optimize the performance of the cochlear implant system 100.

In some alternative examples, the optimal spectral tilt value may not necessarily correspond to the spectral tilt value that results in the highest recognition score achieved by the patient. Rather, the optimal spectral tilt value may correspond to a spectral tilt value resulting in a most comfortable stimulation level and/or a particular cochlear implant system performance level as desired by the patient.

Figure 8:
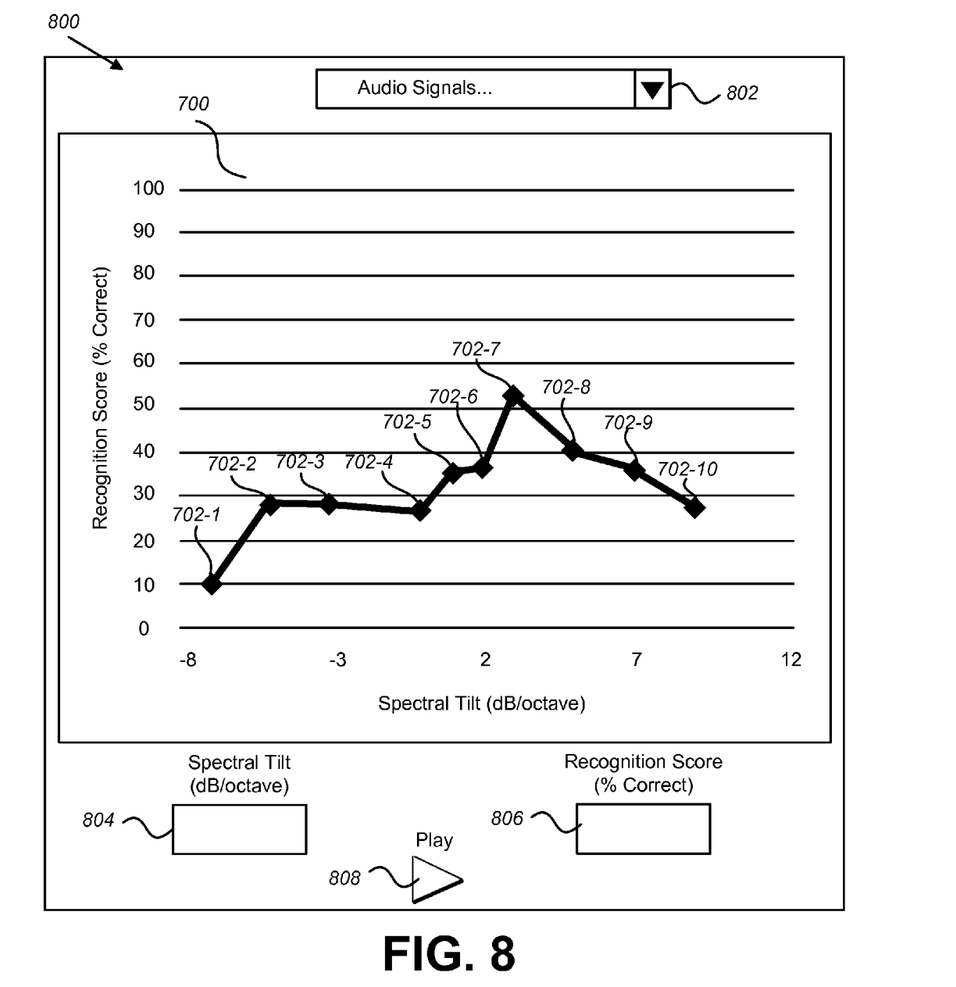
FIG. 8 shows a graphical user interface that may be displayed by a programming device and that is configured to facilitate selection of an optimal spectral tilt value for a particular cochlear implant patient according to principles described herein.

FIG. 8 shows a GUI 800 that may be displayed by programming device 502 and that is configured to facilitate selection of an optimal spectral tilt value for a particular cochlear implant patient. As shown in FIG. 8, GUI 800 may include a depiction of graph 700 so that the clinician or other user thereof may visually see the change in recognition scores that occurs as a result of a change in the spectral tilt.

GUI 800 may further include an audio signal selection menu 802, a spectral tilt input field 804, a recognition score input field 806, and a selectable play icon 808. The audio signal selection menu 802, when selected, may display the names of a number of different audio signals that may applied to the cochlear implant patient. One or more of the audio signals may be configured to exemplify or simulate different one or more listening environments. A clinician or other user may select one of the audio signals for presentation to the cochlear implant patient.

Spectral tilt input field 804 may be configured to facilitate user input of a particular spectral tilt value. Upon selection of the play icon 808, the programming device 502 may direct the sound processor 110 to apply electrical stimulation representative of the selected audio signal in accordance with the specified spectral tilt value. For example, a clinician may input a spectral tilt value of 0 dB/octave into the spectral tilt input field 804 and then select the play icon 808 to direct the sound processor 110 to apply electrical stimulation representative of the selected audio signal to the cochlear implant patient in accordance with the specified spectral tilt value.

One or more tests may then be performed to derive a recognition score, which may be input manually by the clinician, patient, and/or other user into recognition score field 806. The programming device 502 may then store the inputted value and update the graph 700 accordingly. In some alternative examples, the recognition score may be automatically acquired by the programming device 502 in any suitable manner.

Figure 9:
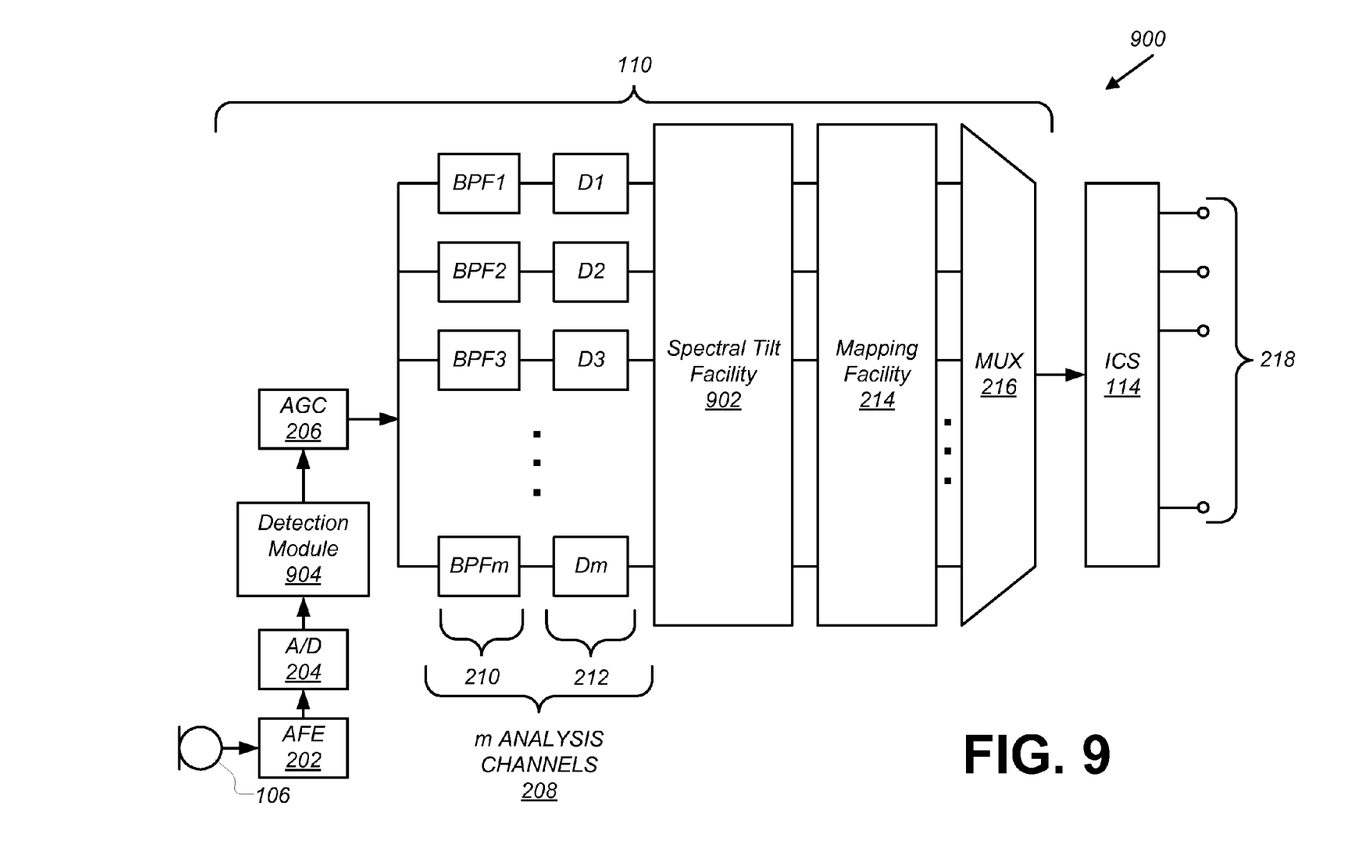
FIG. 9 illustrates a functional block diagram of an exemplary cochlear implant system configured to generate and apply electrical stimulation in accordance with an optimal spectral tilt value according to principles described herein.

FIG. 9 illustrates a functional block diagram of an exemplary cochlear implant system 900 configured to generate and apply electrical stimulation in accordance with an optimal spectral tilt value as determined by programming device 502.

As shown in FIG. 9, a spectral tilt facility 902 may be included within sound processor 110. Spectral tilt facility 902 configured to adjust a spectral tilt of electrical stimulation applied via one or more stimulation channels 218 in accordance with an optimal spectral tilt value. For example, spectral tilt facility 902 may be configured to adjust the spectral tilt in accordance with a measured ability of the patient to recognize at least one attribute of the audio signal, a detected listening environment, and/or any other parameter as may serve a particular application. To this end, spectral tilt facility 902 may include any combination of hardware, software, and/or firmware as may serve a particular application.

To illustrate, spectral tilt facility 902 may adjust one or more gain parameters corresponding to one or more of the stimulation channels 218 so that the spectral tilt corresponding to an input audio signal matches the optimal spectral tilt of the patient as determined by programming device 502. Spectral tilt facility 902 may additionally or alternatively include a pre-determined look up table containing optimal spectral tilt values for a plurality of listening environments. Spectral tilt facility 902 may be configured to match as closely as possible the detected listening environment to one of the listening environments contained within the look-up table and select the corresponding spectral tilt value as the spectral tilt value for the detected listening environment. Spectral tilt facility 902 may additionally or alternatively be configured to measure the spectral tilt in an input audio signal and adjust the spectral tilt to match an optimal spectral tilt corresponding to a patient.

In some examples, spectral tilt facility 902 may direct mapping facility 214 to generate one or more stimulation parameters used to define the electrical stimulation generated by the implantable cochlear stimulator 114 in accordance with optimal spectral tilt value. Implantable cochlear stimulator 114 may then apply electrical stimulation via one or more stimulation channels 218 in accordance with the one or more stimulation parameters.

As mentioned, the optimal value of spectral tilt to improve hearing varies not only from patient to patient but from listening environment to listening environment. For example, the optimal value of spectral tilt for a patient in an ideal listening environment for hearing often differs from the optimal value of spectral tilt in an listening environment characterized by background noise. Because various listening environments have characteristic, recognizable, and detectable patterns, the systems and methods described herein may be configured to adjust upon detection of certain listening environments.

To facilitate detection of a listening environment, sound processor 110 may include a detection module 904. Detection module 904 may detect a listening environment of a patient using any process or heuristic as may serve a particular application. For example, detection module 904 may compare one or more characteristics of the input audio signal to one or more characteristics corresponding to various listening environments. As shown in FIG. 9, detection module 904 may be disposed in between A/D converter 204 and AGC module 206. Additionally or alternatively, detection module 904 may follow band pass filters 210 and energy detection stages 212. As mentioned, spectral tilt facility 902 may be configured to adjust the spectral tilt in accordance with a detected listening environment.

Figure 10:
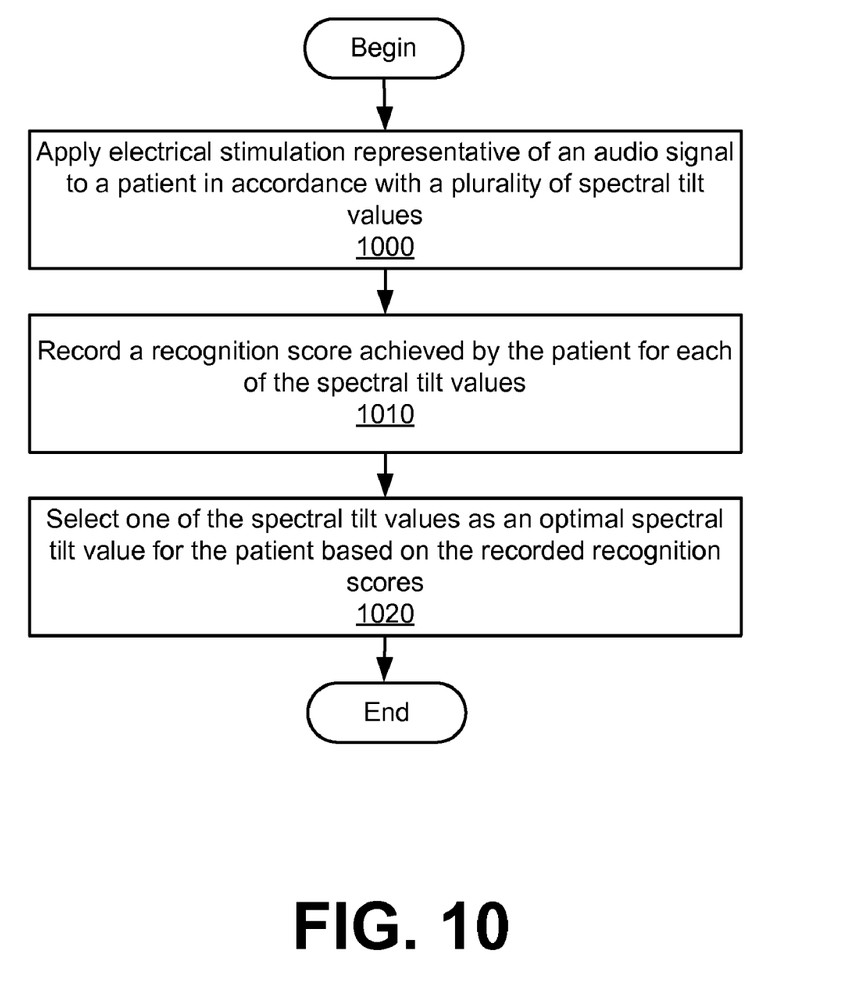
FIG. 10 illustrates an exemplary method of optimizing a spectral tilt value for a cochlear implant patient according to principals described herein.

FIG. 10 illustrates an exemplary method of optimizing a spectral tilt value for a cochlear implant patient. While FIG. 10 illustrates exemplary steps according to one embodiment, other embodiments may omit, add to, reorder, and/or modify any of the steps shown in FIG. 10. Any of the steps described in FIG. 10 may be performed by sound processor 110, implantable cochlear stimulator 114, programming device 502, and/or any other component included within system 500 as may serve a particular application.

In step 1000, electrical stimulation representative of an audio signal is applied to a cochlear implant patient in accordance with a plurality of spectral tilt values. The electrical stimulation may be applied in accordance with the spectral tilt values in any of the ways described herein.

In step 1010, a recognition score achieved by the patient for each of the spectral tilt values is recorded. The recognition core corresponds to an ability of the patient to recognize at least one attribute of the audio signal applied in accordance with each of the spectral tilt values and may be measured and/or recorded in any of the ways described herein.

In step 1020, one of the spectral tilt values is selected as an optimal spectral tilt value for the patient based on the recorded recognition scores. In some examples, the optimal spectral tilt value corresponds to a highest recognition score achieved by the patient.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A method comprising:
    applying electrical stimulation representative of an audio signal to a patient by way of at least one electrode included in a plurality of electrodes disposed within a cochlea of the patient in accordance with a spectral tilt value that defines a single constant slope of a linear gain-to-electrode function corresponding to the plurality of electrodes as a whole; and
    optimizing the spectral tilt value in response to a measured ability of the patient to recognize at least one attribute of the audio signal.

2. The method of claim 1, wherein the optimizing of the spectral tilt value comprises:
    generating a plurality of spectral tilt values each representing a distinct slope of the linear gain-to-electrode function;
    recording a recognition score achieved by the patient for each of the plurality of spectral tilt values, the recognition score corresponding to an ability of the patient to recognize at least one attribute of the audio signal applied in accordance with each of the spectral tilt values; and
    selecting one of the spectral tilt values as an optimal spectral tilt value for the patient based on the recorded recognition scores.

3. The method of claim 2, wherein the selecting of one of the spectral tilt values as the optimal spectral tilt value comprises selecting a spectral tilt value corresponding to a maximum recognition score achieved by the patient.

4. The method of claim 2, wherein the generating of the plurality of the spectral tilt values comprises adjusting a plurality of gain parameters each corresponding to a stimulation channel configured to apply at least a portion of the electrical stimulation to the patient.

5. The method of claim 1, wherein the audio signal comprises speech.

6. The method of claim 1, wherein the measured ability of the patient to recognize at least one attribute of the audio signal comprises a speech recognition score.

7. The method of claim 1, wherein the audio signal is representative of a listening environment of the user.

8. The method of claim 1, wherein the optimizing of the spectral tilt value comprises:
    detecting a listening environment of the user; and
    adjusting the spectral tilt value in accordance with the detected listening environment.

9. A method comprising:
    applying electrical stimulation representative of an audio signal to a cochlear implant patient by way of at least one electrode included in a plurality of electrodes disposed within a cochlea of the patient in accordance with a plurality of spectral tilt values each defining a distinct single constant slope of a linear gain-to-electrode function corresponding to the plurality of electrodes as a whole;
    recording a recognition score achieved by the patient for each of the spectral tilt values, the recognition score corresponding to an ability of the patient to recognize at least one attribute of the audio signal applied in accordance with each of the spectral tilt values; and
    selecting one of the spectral tilt values as an optimal spectral tilt value for the patient based on the recorded recognition scores.

10. The method of claim 9, wherein the selecting of one of the spectral tilt values as the optimal spectral tilt value comprises selecting a spectral tilt value corresponding to a maximum recognition score achieved by the patient.

11. The method of claim 9, further comprising generating the plurality of the spectral tilt values by adjusting a plurality of gain parameters each corresponding to a stimulation channel configured to apply at least a portion of the electrical stimulation to the patient.

12. The method of claim 9, wherein the audio signal comprises speech.

13. The method of claim 9, wherein the recognition score comprises a speech recognition score.

14. The method of claim 9, wherein the audio signal is representative of a listening environment of the user.

15. The method of claim 9, further comprising:
    detecting a listening environment of the user; and
    adjusting the spectral tilt value in accordance with the detected listening environment.

16. A system comprising:
    an implantable cochlear stimulator configured to apply electrical stimulation representative of an audio signal to a patient by way of at least one electrode included in a plurality of electrodes disposed within a cochlea of the patient in accordance with a spectral tilt that defines a single constant slope of a linear gain-to-electrode function corresponding to the plurality of electrodes as a whole; and
    a sound processor communicatively coupled to the implantable cochlear stimulator and configured to adjust the spectral tilt in response to a measured ability of the patient to recognize at least one attribute of the audio signal.

17. The system of claim 16, further comprising a programming device communicatively coupled to the sound processor and configured to display a graphical user interface configured to facilitate adjustment of the spectral tilt.

18. The system of claim 17, wherein the programming device is further configured to:
    direct the sound processor to generate a plurality of spectral tilt values each representing a distinct slope of the linear gain-to-electrode function;
    record a recognition score achieved by the patient for each of the plurality of spectral tilt values; and
    select one of the spectral tilt values as an optimal spectral tilt value for the patient based on the recorded recognition scores.

* * * * *